(12) United States Patent
Logan (10) Patent No.: US 8,616,212 B1
(45) Date of Patent: Dec. 31, 2013

(54) VAS DEFERENS OR FALLOPIAN TUBES VALVE SYSTEM

(76) Inventor: John R. Logan, Lafayette, GA (US)

(*) Notice: Subject to any disclaimer, the term of this patent is extended or adjusted under 35 U.S.C. 154(b) by 53 days.

(21) Appl. No.: 13/296,283

(22) Filed: Nov. 15, 2011

(51) Int. Cl.
*A61F 6/06* (2006.01)
*A61B 8/14* (2006.01)
*A61M 29/00* (2006.01)

(52) U.S. Cl.
USPC .................. 128/831; 600/467; 606/193

(58) Field of Classification Search
USPC .......... 128/842, 843; 600/459, 417, 425, 437, 600/439, 462, 461, 463, 467; 604/9; 606/158, 157, 151, 1, 193–194
See application file for complete search history.

(56) References Cited

U.S. PATENT DOCUMENTS

| 3,731,670 | A | * | 5/1973 | Loe ............................ 600/30 |
| 3,815,578 | A | * | 6/1974 | Bucalo ...................... 128/843 |
| 4,325,377 | A | * | 4/1982 | Boebel ...................... 606/142 |
| 5,425,739 | A | * | 6/1995 | Jessen ....................... 606/155 |
| 2011/0067705 | A1 | * | 3/2011 | Kennedy .................... 128/843 |

* cited by examiner

*Primary Examiner* — Patricia Bianco
*Assistant Examiner* — Tarla Patel (57) ABSTRACT

The Vas Deferens or Fallopian tubes valve system incorporates a small valve in line with either the Vas Deferens or the Fallopian tube in order to open or close fluid communication therein, and effectively a form of birth control. The valve is installed on either one of the Fallopian tubes or Vas Deferens, and is manually or remotely controlled. The small valve is manually controlled via an arm that can be manually rotated to open or close the valve seated there under. A magnetic version of the small valve incorporates magnets on the arm in order to induce motion of the arm upon focusing a magnetic field upon the valve. A remotely operable valve utilizes a solenoid and radio receiver to remotely operate the small valve.

5 Claims, 7 Drawing Sheets

VAS DEFERENS OR FALLOPIAN TUBES VALVE SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of Birth control, more specifically, a valve system for use with the Vas Deferens as well as the Fallopian tubes.

Male and female birth control have evolved in the last 50 years. According to Wikipedia, the first Vasectomy was performed in 1989. Since then, there have been cases where the vas deferens become re-connected and unplanned children have resulted. Moreover, some individuals seek to undo a Vasectomy as needed in order to procreate when the time is right. In some situations it may be ideal to selectively block off or unblock the Vas Deferens or Fallopian tubes in order to effectively act as a form of birth control. The device of the present application seeks to overcome the limitations of a traditional Vasectomy or other forms of birth control by providing a valve system that can selectively block or unblock the Vas Deferens or the Fallopian tubes.

B. Discussion of the Prior Art

As will be discussed immediately below, no prior art discloses a small valve that is installed on the Vas Deferens or Fallopian tubes and which can selectively open or close fluid communication along the Vas Deferens or Fallopian tubes thereby providing selection of temporary sterilization versus fertile performance; wherein both Vas Deferens or Fallopian tubes are provided with a small valve that is installed in-line and which can be manually operated or remotely operable; wherein the manually operated small valve is simply a ball type, gate type, or slide type valve that has an arm that is manually rotated to open or close the valve; wherein a remotely operable valve shall include a magnetic solenoid and radio receiver that can be controlled wirelessly in order to open or close the valve without requiring additional surgery.

The Bucalo Patent (U.S. Pat. No. 3,707,957) discloses a vas valve adapted to be situated in a human vas deferens for closing and opening the latter. However, the valve is not adapted for use with either the Vas Deferens or the Fallopian tube, and also does not disclose a remotely operable valve for non-surgical control of the valve.

The Rogers Patent (U.S. Pat. No. 3,820,528) discloses a valve assembly for use in the tubes of the vas deferens. Again, the valve is specifically suited for use with the vas deferens and not adapted for use with the fallopian tube.

The Thorsgard Patent (U.S. Pat. No. 4,682,592) discloses a device and method of male sterilization that is both reversible and involves only non-surgical procedures that involves inserting a plug through the urethra to block the passage of sperm and the consequent fertilization during intercourse. However, the device is not a valve that can be manually or remotely operated to open and close fluid communication to either a vas deferens or a fallopian tube.

The Robinson Patent (U.S. Pat. No. 3,699,957) discloses a prosthetic device for reversibly blocking semen flow through the vas deferens. Again, the device is not a valve that can be manually or remotely operated to open and close fluid communication to either a vas deferens or a fallopian tube.

The Summers Patent (U.S. Pat. No. 3,750,194) discloses an apparatus and method for reversibly closing a natural or implanted body passage. However, the apparatus is not a valve specifically suited for in-line use on a fallopian tube or vas deferens in order to selectively open or close fluid communication therein.

The Hengesbach Patent (U.S. Pat. No. Des. 331,964) illustrates an ornamental design for a combined flow control valve and spray wand tube, which does not depict a valve for use with a vas deferen or fallopian tube.

While the above-described devices fulfill their respective and particular objects and requirements, they do not describe a small valve that is installed on the Vas Deferens or Fallopian tubes and which can selectively open or close fluid communication along the Vas Deferens or Fallopian tubes thereby providing selection of temporary sterilization versus fertile performance; wherein both Vas Deferens or Fallopian tubes are provided with a small valve that is installed in-line and which can be manually operated or remotely operable; wherein the manually operated small valve is simply a ball type, gate type, or slide type valve that has an arm that is manually rotated to open or close the valve; wherein a remotely operable valve shall include a magnetic solenoid and radio receiver that can be controlled wirelessly in order to open or close the valve without requiring additional surgery. In this regard, the Vas Deferens or Fallopian tubes valve system departs from the conventional concepts and designs of the prior art.

SUMMARY OF THE INVENTION

The Vas Deferens or Fallopian tubes valve system incorporates a small valve in line with either the Vas Deferens or the Fallopian tube in order to open or close fluid communication therein, and effectively a form of birth control. The valve is installed on either one of the Fallopian tubes or Vas Deferens, and is manually or remotely controlled. The small valve is manually controlled via an arm that can be manually rotated to open or close the valve seated there under. A magnetic version of the small valve incorporates magnets on the arm in order to induce motion of the arm upon focusing a magnetic field upon the valve. A remotely operable valve utilizes a solenoid and radio receiver to remotely operate the small valve.

It is an object of the invention to provide a valve system that is installed in-line with either a Vas Deferens or a Fallopian tube and which can open or close fluid communication therein, and which is effectively a form of birth control.

A further object of the invention is to provide a valve system that can be manually operated or remotely operated.

A further object of the invention is to provide a valve system that can be controlled upon introducing a magnetic field onto the valve system.

A further object of the invention is to provide a remotely operated small valve that does not require surgery in order to control the valve, and which moves the valve upon receiving a predefined radio frequency.

A further object of the invention is to provide a valve that can be adapted for use with either the Fallopian tube or the Vas Deferens, and which is only differentiated by the internal diameter of the valve with respect to the Fallopian tube versus the Vas Deferens.

These together with additional objects, features and advantages of the Vas Deferens or Fallopian tubes valve system will be readily apparent to those of ordinary skill in the art upon reading the following detailed description of presently preferred, but nonetheless illustrative, embodiments of the Vas Deferens or Fallopian tubes valve system when taken in conjunction with the accompanying drawings.

In this respect, before explaining the current embodiments of the Vas Deferens or Fallopian tubes valve system in detail, it is to be understood that the Vas Deferens or Fallopian tubes valve system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the Vas Deferens or Fallopian tubes valve system.

It is therefore important that the claims be regarded as including such equivalent construction insofar as they do not depart from the spirit and scope of the Vas Deferens or Fallopian tubes valve system. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to the preferred embodiment of the present invention, examples of which are illustrated in FIGS. 1-6B. A Vas Deferens or Fallopian tubes valve system 100 (hereinafter invention) includes a small valve 101 that is installed in-line on a Vas Deferens 120 or Fallopian tube 130. It shall be noted that the term valve 101 is being used to refer to one of a multitude of valve-styles comprising a ball-type valve, a gate-type valve, or a slide-type valve.

It shall be noted that the valve 101 includes an inner diameter 101A, which shall vary depending upon use with either the Vas Deferens 120 or the Fallopian tubes 130. The inner diameter 101A shall range from 0.5-1.2 centimeters when in use on the Fallopian tube 130; whereas the inner diameter 101A shall have a range from 0.3-0.5 centimeters when in use on the Vas Deferens 120.

The valve 101 shall be further defined with a length 101B, which shall range from 1.0-1.5 centimeter, and regardless of use on the Vas Deferens 120 or the Fallopian tubes 130. The valve 101 has an outer width 101C ranging from 0.6-0.8 centimeters, and regardless of use on the Vas Deferens 120 or the Fallopian tubes 130.

The valve 101 includes a valve housing 102 from which the valve 101 rotates. It shall be noted that the means of rotating the valve 101 varies depending upon the style of valve used, which will be described in more detail below.

Figure 1:
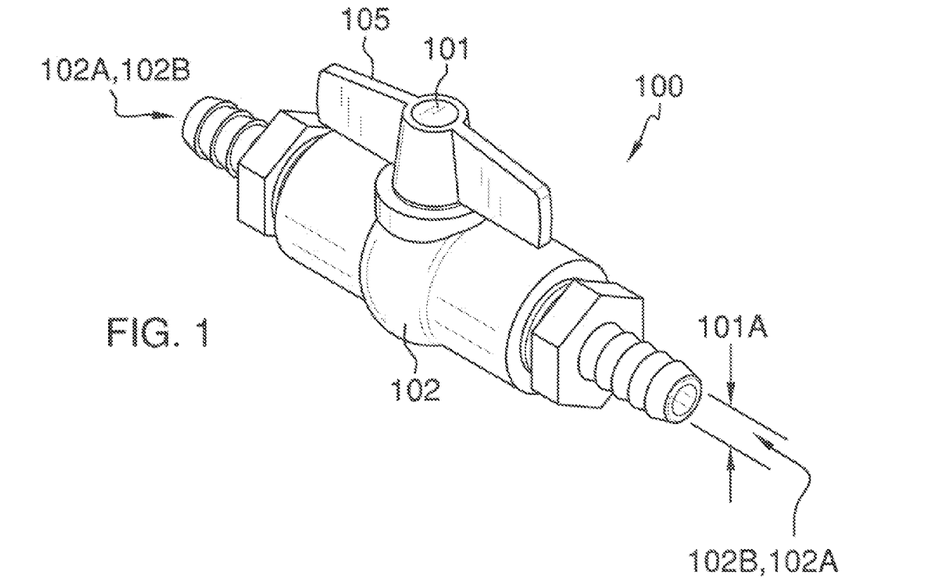
FIG. 1 illustrates a perspective view of the valve by itself in which an arm is provided thereon for manual operation thereof.
Figure 2:
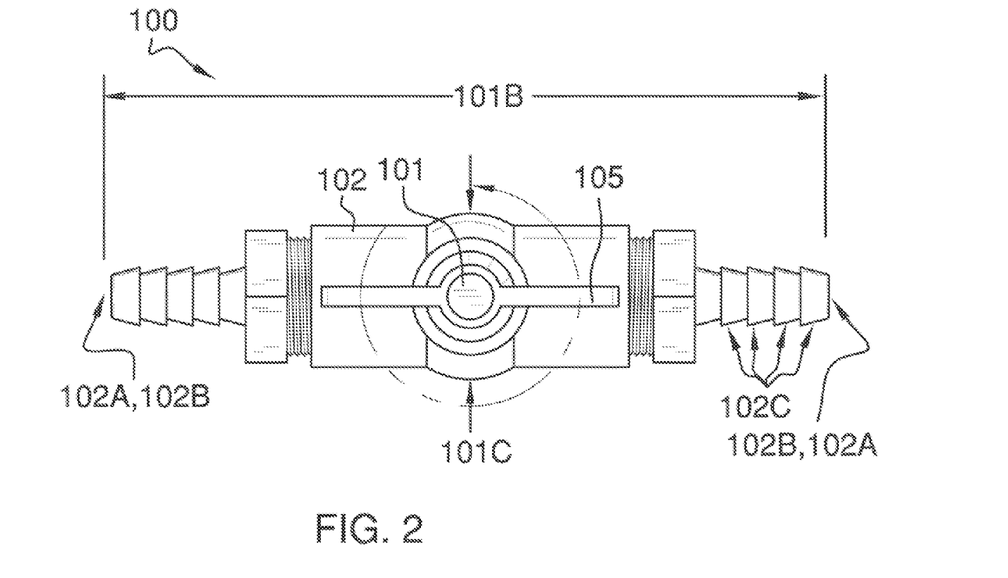
FIG. 2 illustrates a top view of the valve in which a rotational arrow indicates rotational movement of the arm with respect to the valve seat.
Figure 3A:
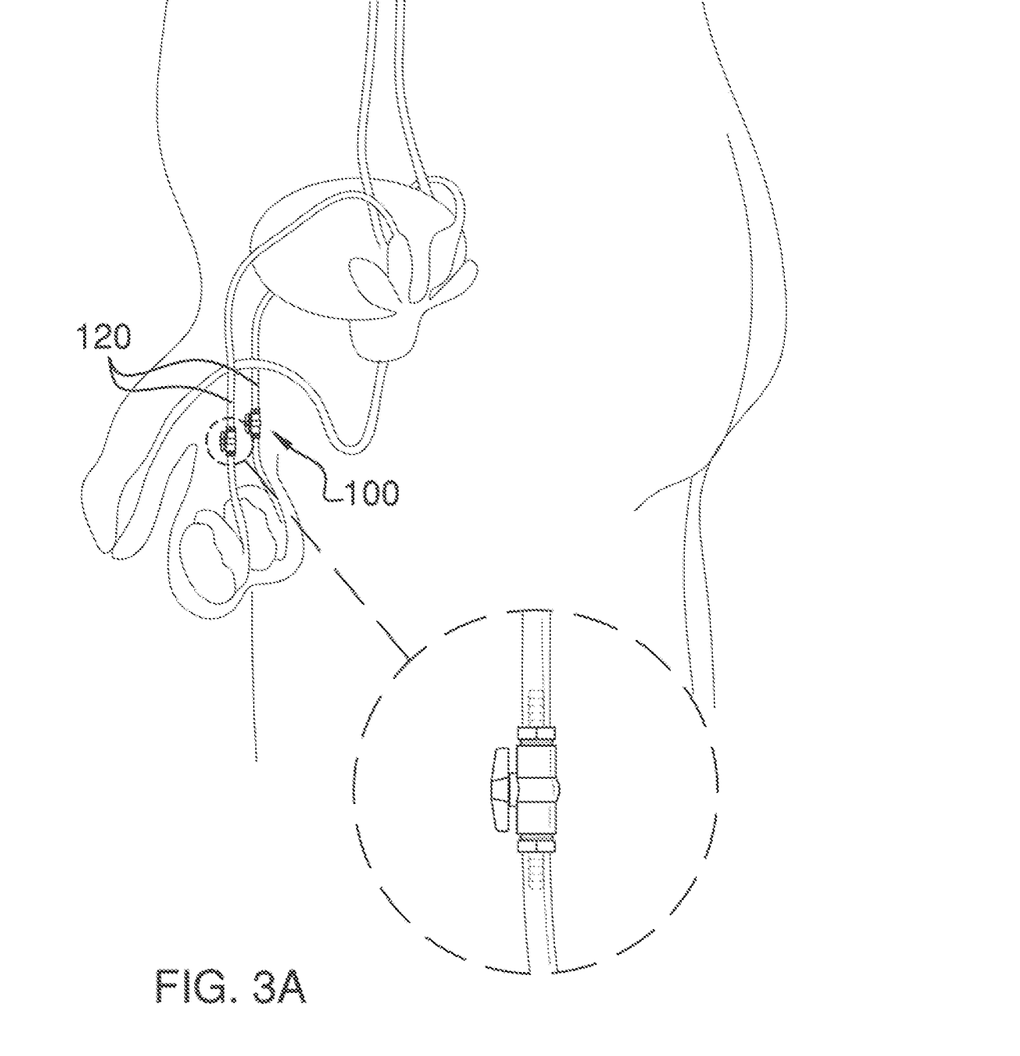
FIG. 3A illustrates a view of the valve system installed on a vas deferens of a male patient, and a close up of one valve depicting the in-line orientation therein.
Figure 3B:
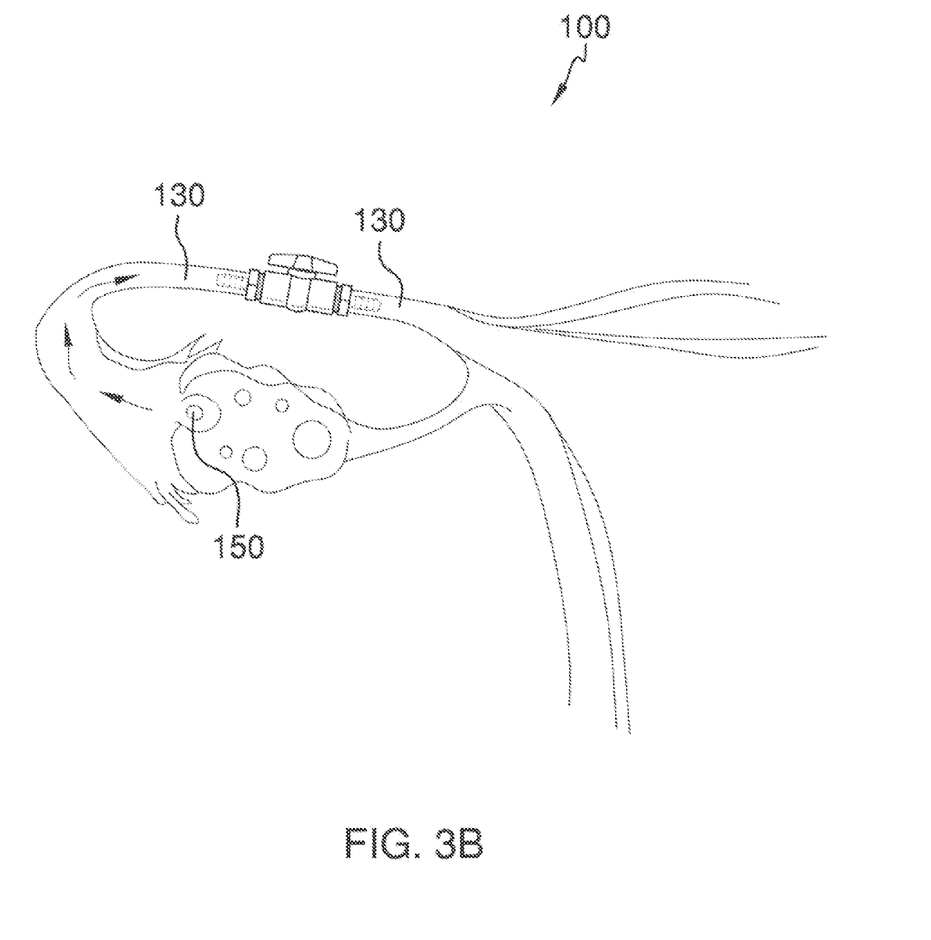
FIG. 3B illustrates a view of the valve system installed on a Fallopian tube, which can open or close off fluid communication therein.
Figure 4A:
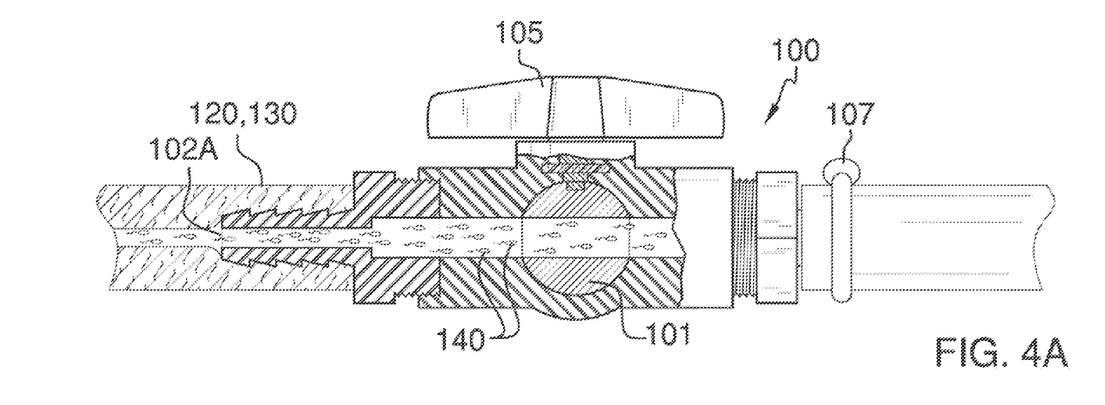
FIG. 4A illustrates a cross-sectional view of the valve installed on either a Fallopian tube or a Vas Deferens in which the valve is manually operated and in an open configuration.

The valve housing 102 is further defined with an inlet 102A and an outlet 102B. Located at the inlet 102A and the outlet 102B are barbs 102C, which are used to secure the valve 101 in-line with the Vas Deferens 120 or the Fallopian tubes 130. The inner diameter 101A of the valve 101 is referring to the inner diameter of the inlet 102A and the outlet 102B. It shall be noted that the inlet 102A and the outlet 102B slide into a portion of the respective end of the Vas Deferens 120 or Fallopian tubes 130. Furthermore, the barbs 102C help to secure the invention 100 in place and in-line with the respective vas Deferens and Fallopian tubes. Referring to FIG. 4A, the invention 100 may include the use of a strap 107 to encircle the exterior of the Fallopian tube 130 or Vas Deferens 120 in order to provide an additional securing means of the invention 100 thereon.

The premise behind the use of the valve 101 is to block the passageway of sperm 140 through either the Vas Deferens 120 or the Fallopian tubes 130, which effectively acts as a form of birth control by denying access of the sperm 140 to an egg 150.

Figure 4B:
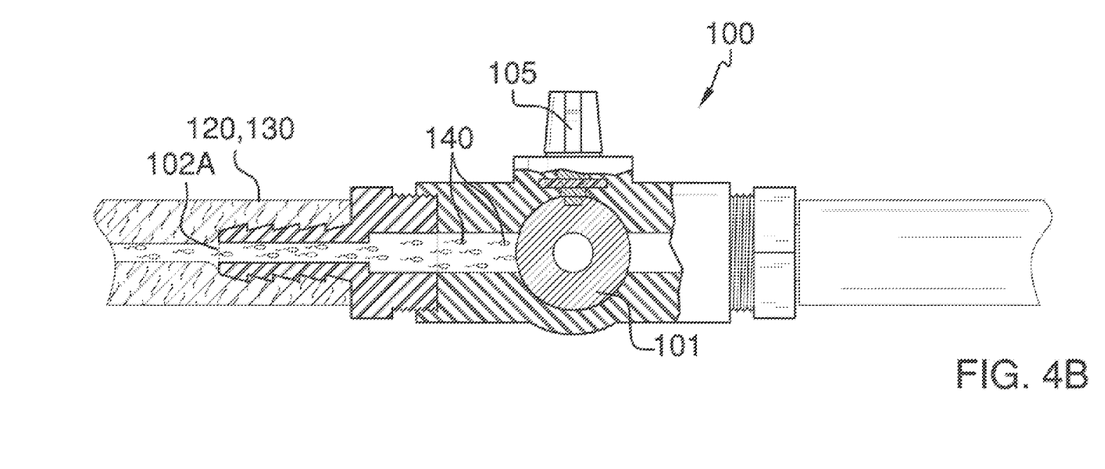
FIG. 4B illustrates a cross-sectional view in which the valve is in a closed position thereby blocking sperm from passing through either the Fallopian tube or Vas Deferens.

Referring to FIGS. 4A and 4B, the valve 101 as depicted is manually operated, which requires a surgical procedure each time an end user elects to change the position of the valve 101 as installed on either the Vas Deferens 120 or the Fallopian tubes 130. In this situation, the valve 101 includes an arm 105 that can rotate the valve 101 internally, and with respect to the valve housing 102 thereby resulting in an open or closed position. In referring to FIG. 4A, the valve 101 is in an open position thereby enabling fluid communication between the inlet 102A and the outlet 102B. In referring to FIG. 4B, the valve 101 is in a closed state, which results in no fluid communication between the inlet 102A and the outlet 102B. The fluid communication of the invention 100 shall dictate whether sperm 140 can or cannot pass through the valve 101.

Figure 5A:
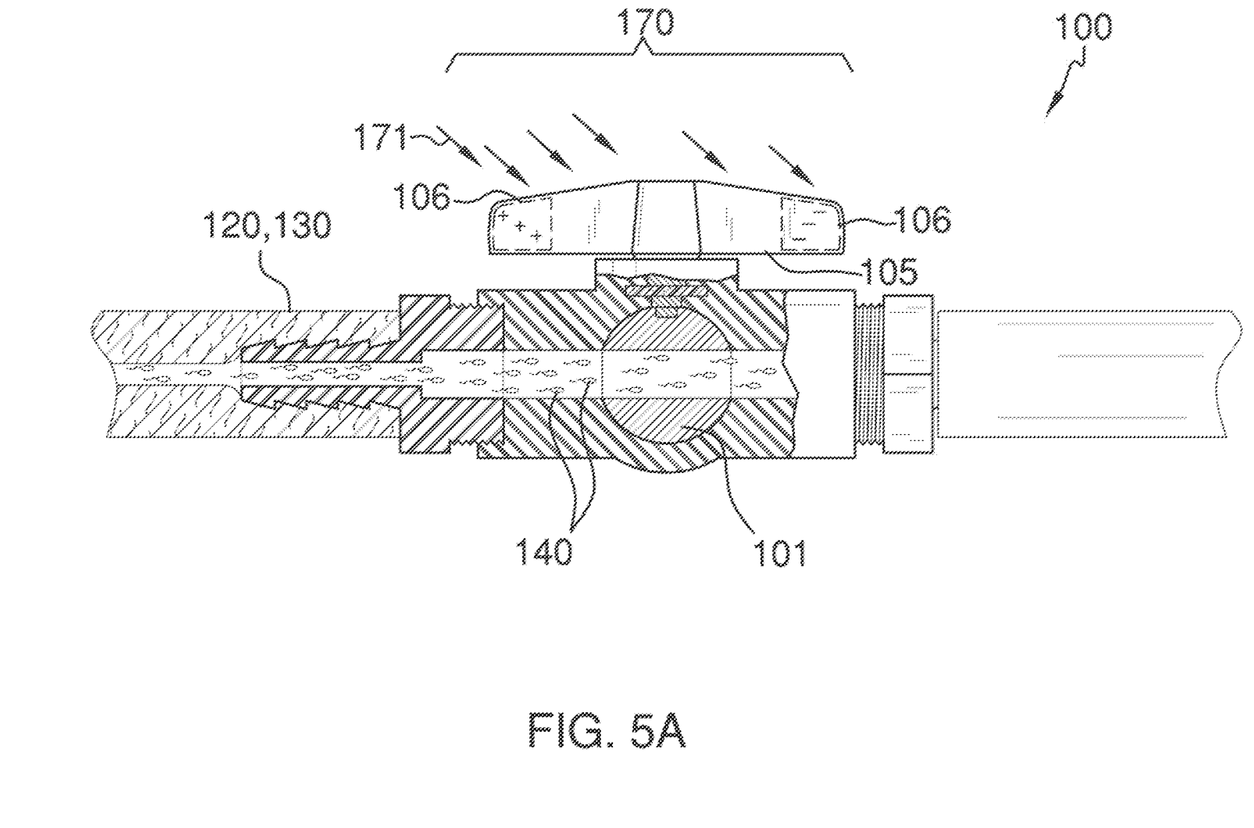
FIG. 5A illustrates a cross-sectional view of a valve having magnets built into the arm, which are rotated upon introduction of a magnetic field as denoted by the multitude of arrows, and in which the valve is in an open configuration.
Figure 5B:
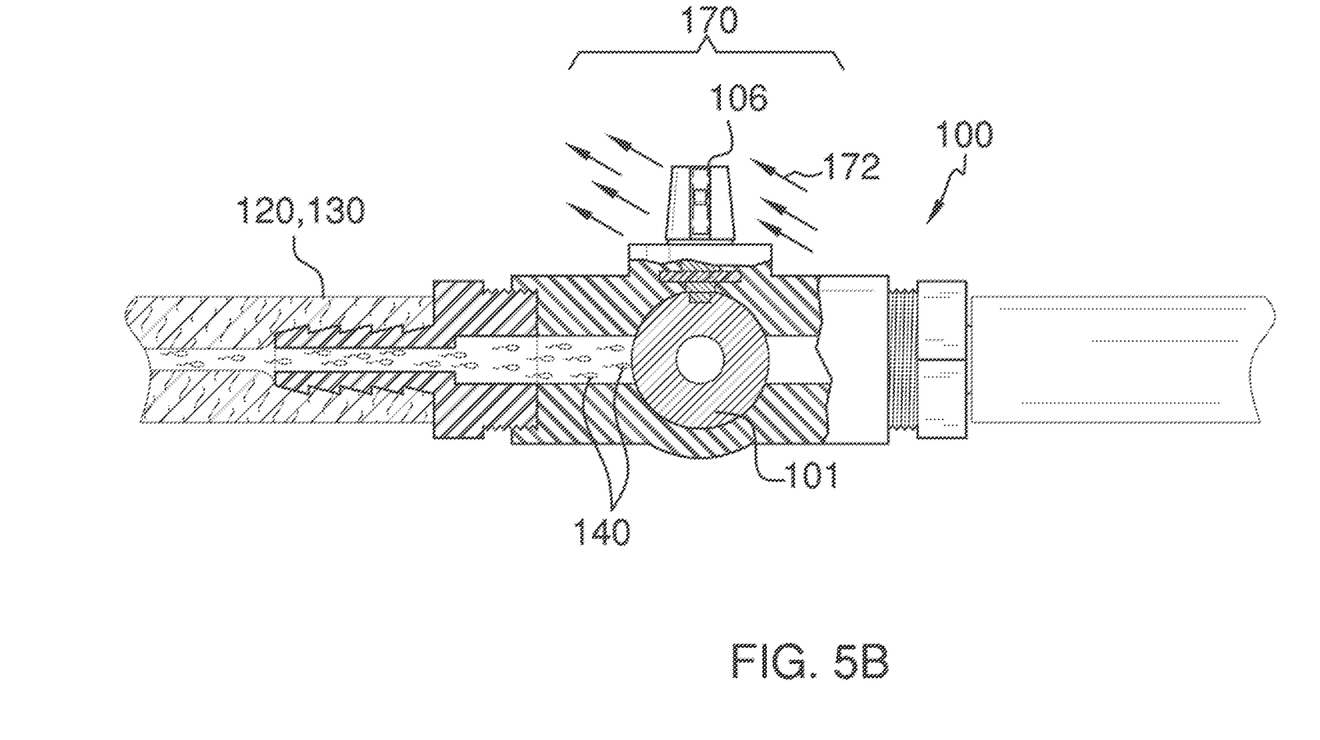
FIG. 5B illustrates a cross-sectional view of the magnetically operated valve in which the valve is in a closed position as a result of a second magnetic field denoted by the multitude of arrows.

Referring to FIGS. 5A and 5B, the valve 101 as depicted is a magnetically operable valve, which may or may not require a surgical procedure to change the position of the valve 101. The only change to the valve 101 in FIGS. 5A and 5B is the inclusion of magnets 106 in distal ends of the arm 105. The magnets 106 are in opposing magnetic alignment, which is denoted by the "+" and "−" denoted thereon. The magnets 106 are located at distal ends of the arm 105, and shall rotate the arm 105 and the valve 101 seated therein upon exposure to a specific magnetic field 170. The term magnetic field is being used to describe a focused field of magnetism, which depending on direction shall influence the magnets 106 to rotate the valve 101 to either an open position or a closed position.

Referring to FIG. 5A, the magnetic field 170 is directed in an open direction 171, which causes the magnets 106 to open the valve 101. Referring to FIG. 5B, the magnetic field 170 is directed in a closed direction 172, which causes the magnets 106 to close the valve 101.

It shall be noted that the invention 100 as depicted in FIGS. 5A-5B may in the alternative be manually operated to open or close the valve 101. It shall be further noted that to manually operate the valve 101 shall require a surgical procedure.

Figure 6A:
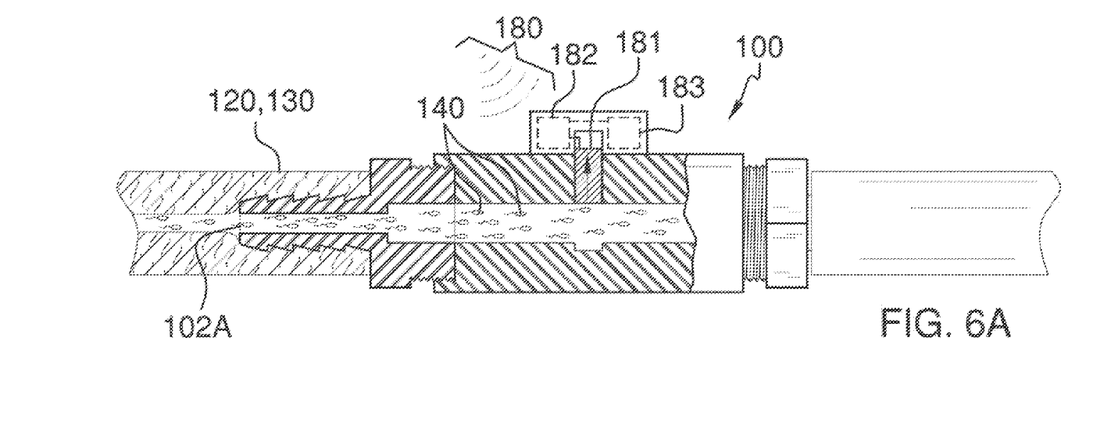
FIG. 6A illustrates a cross-sectional view of a solenoid valve that is remotely operated via a radio frequency and in which said valve is installed in-line on either a Fallopian tube or Vas Deferens, and is depicted in an open position.
Figure 6B:
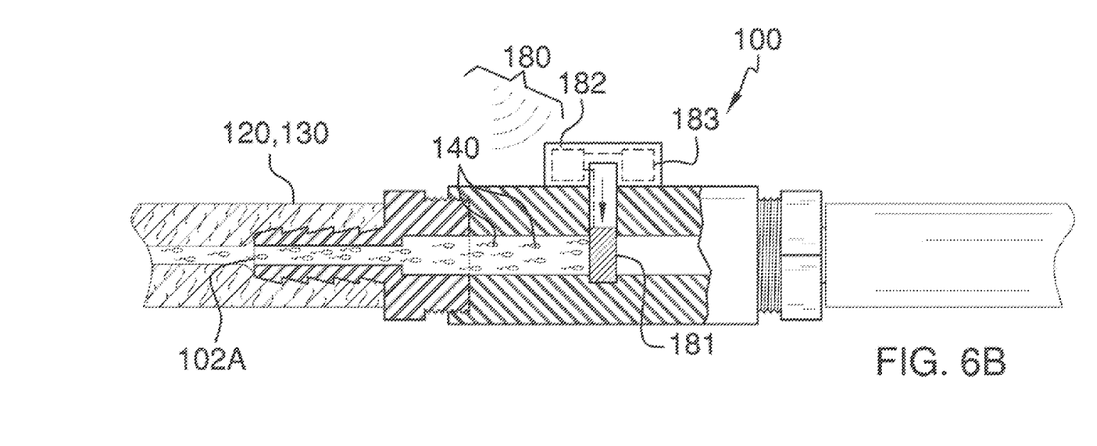
FIG. 6B illustrates a cross-sectional view of the remotely operated valve in a closed position upon receiving a radio frequency.

Referring to FIGS. 6A-6B, the valve 101 as depicted is a remotely operable valve, which utilizes a radio frequency 180 to control a solenoid 181 seated within the valve housing 101. In the embodiment of FIGS. 6A-6B, the valve is actually the solenoid 181 traveling from an open position (see FIG. 6A) to a closed position (see FIG. 6B). A radio receiver 182 and a powering means 183 are included with the solenoid 181, and control and power the solenoid 181, respectively. Upon detection of the radio frequency 180, the radio receiver 182 shall move the solenoid 181 to an open position (FIG. 6A) or to a closed position (FIG. 6B). The advantage of the embodiment of the invention 100 as depicted in FIGS. 6A-6B is the ability to control the valve 101 remotely, and without requiring a surgical procedure to change the valve orientation.

In all embodiments of the invention 100 it shall be noted that an initial surgical procedure shall be required in order to install the invention 100 in-line with the Vas Deferens 120 or the Fallopian tubes 130. Depending upon whether the valve 101 is manually operated, magnetically operated, or remotely operated shall dictate the necessity for additional surgical procedures.

With respect to the above description, it is to be realized that the optimum dimensional relationship for the various components of the invention 100, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 100.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A Vas Deferens or Fallopian tubes valve system comprising:
 a valve installed in-line and configured for use with either a vas Deferens or Fallopian tube in order to open or close off fluid communication therein as a means of birth control by controlling travel of sperm or an egg there through;
 wherein the valve includes a valve housing defined with an inlet and an outlet; wherein both the inlet and the outlet are provided with barbs in securing the respective end of the Fallopian tube or Vas Deferens thereon;
 wherein a strap is added on either end of the valve, and encircles an exterior of the Fallopian tube or Vas Deferens as an added means of securing the valve thereon;
 wherein the inlet and outlet have an inner diameter ranging from 0.5-1.2 centimeters when in use on the Fallopian tube; wherein the inlet and outlet have an inner diameter ranging from 0.3-0.5 centimeters when in use on the Vas Deferens;
 wherein the valve includes an arm that is manually rotated to open or close the valve.

2. The Vas Deferens or Fallopian tubes valve system as described in claim 1 wherein the arm includes magnets on distal ends, which can rotate the arm upon exposure to a specific magnetic field.

3. The Vas Deferens or Fallopian tubes valve system as described in claim 2 wherein the magnets are in opposing magnetic alignment.

4. A Vas Deferens or Fallopian tubes valve system comprising:
 a valve installed in-line and configured for use with either a vas Deferens or Fallopian tube in order to open or close off fluid communication therein as a means of birth control by controlling travel of sperm or an egg there through;
 wherein the valve includes a valve housing defined with an inlet and an outlet; wherein both the inlet and the outlet are provided with barbs in securing the respective end of the Fallopian tube or Vas Deferens thereon;
 wherein a strap is added on either end of the valve, and encircles an exterior of the Fallopian tube or Vas Deferens as an added means of securing the valve thereon;
 wherein the inlet and outlet have an inner diameter ranging from 0.5-1.2 centimeters when in use on the Fallopian tube; wherein the inlet and outlet have an inner diameter ranging from 0.3-0.5 centimeters when in use on the Vas Deferens;
 wherein the valve is a ball-valve style, and includes an arm that is manually rotated to open or close the valve;
 wherein the arm includes magnets on distal ends, which can rotate the arm upon exposure to a specific magnetic field;
 wherein the magnets are in opposing magnetic alignment.

5. A Vas Deferens or Fallopian tubes valve system comprising:

a valve installed in-line and configured for use with either a vas Deferens or Fallopian tube in order to open or close off fluid communication therein as a means of birth control by controlling travel of sperm or an egg there through;

wherein the valve includes a valve housing defined with an inlet and an outlet; wherein both the inlet and the outlet are provided with barbs in securing the respective end of the Fallopian tube or Vas Deferens thereon;

wherein a strap is added on either end of the valve, and encircles an exterior of the Fallopian tube or Vas Deferens as an added means of securing the valve thereon;

wherein the inlet and outlet have an inner diameter ranging from 0.5-1.2 centimeters when in use on the Fallopian tube; wherein the inlet and outlet have an inner diameter ranging from 0.3-0.5 centimeters when in use on the Vas Deferens;

wherein the valve includes a solenoid that is remotely operable upon reception of a radio frequency via a radio receiver in wired communication with said solenoid.

* * * * *